(12) United States Patent
Kyburz et al.

(10) Patent No.: US 7,217,112 B2
(45) Date of Patent: May 15, 2007

(54) MOLD FOR INTRAOCULAR LENS

(75) Inventors: Gene Theodore Kyburz, Pardeeville, WI (US); Faezeh M. Sarfarazi, Carlsbad, CA (US)

(73) Assignee: Faezeh Mona Sarfarazi, Carlsbad, CA (US)

( * ) Notice: Subject to any disclaimer, the term of this patent is extended or adjusted under 35 U.S.C. 154(b) by 173 days.

(21) Appl. No.: 10/445,762

(22) Filed: May 27, 2003

(65) Prior Publication Data

US 2004/0238980 A1    Dec. 2, 2004

(51) Int. Cl.
*B29D 11/00* (2006.01)
(52) U.S. Cl. .................. 425/117; 425/588; 425/808
(58) Field of Classification Search ............... 425/117, 425/188, 468, 588, 808; 249/177; 264/2.7
See application file for complete search history.

(56) References Cited

U.S. PATENT DOCUMENTS

| 3,971,841 | A | | 7/1976 | Rubinstein | |
|---|---|---|---|---|---|
| 4,836,960 | A | | 6/1989 | Spector et al. | |
| 5,275,623 | A | | 1/1994 | Sarfarazi | |
| 5,762,836 | A | * | 6/1998 | Bos et al. | 264/1.7 |
| 5,904,746 | A | | 5/1999 | Okada | |
| 6,096,078 | A | | 8/2000 | McDonald | |
| 6,423,094 | B1 | | 7/2002 | Sarfarazi | |
| 6,488,708 | B2 | | 12/2002 | Sarfarazi | |
| 6,537,316 | B1 | | 3/2003 | Chambers | |
| 6,769,900 | B2 | * | 8/2004 | Murphy et al. | 425/468 |
| 6,939,486 | B2 | * | 9/2005 | DeRyke et al. | 264/1.7 |
| 2001/0007513 | A1 | | 7/2001 | Koshimizu et al. | |
| 2002/0173847 | A1 | | 11/2002 | Pham et al. | 623/6.26 |
| 2003/0018384 | A1 | * | 1/2003 | Valyunin et al. | 623/6.34 |

FOREIGN PATENT DOCUMENTS

| EP | 0875354 B1 | 10/2002 |
|---|---|---|
| WO | WO 2004/010905 A2 | 2/2004 |
| WO | WO 2004/106045 A1 | 12/2004 |

* cited by examiner

*Primary Examiner*—Donald Heckenberg
(74) *Attorney, Agent, or Firm*—DLA Piper US LLP

(57) ABSTRACT

The invention is a mold and method for using the mold to make a multi-stage intraocular lens. The mold is provided with a gate in fluid communication with a lens portion and/or haptic portion of the mold core. In addition, a gasket is provided around the mold core. As molding material is introduced into the mold via the gate, a vacuum is drawn around and through the gasket to evacuate air trapped in the mold core and to help pull the material through the mold core.

29 Claims, 8 Drawing Sheets

MOLD FOR INTRAOCULAR LENS

CROSS-REFERENCE TO RELATED APPLICATIONS

None.

STATEMENT REGARDING FEDERALLY SPONSORED RESEARCH OR DEVELOPMENT

Not Applicable.

APPENDIX

Not Applicable.

BACKGROUND OF THE INVENTION

1. Field of the Invention

This invention relates generally to molds and, more particularly, to a mold for a multi-stage intraocular lens.

2. Related Art

Multi-lens intraocular lenses have been disclosed in U.S. Pat. No. 6,488,708 B1 issued Dec. 3, 2002 ("the '708 patent"). Prior to the invention disclosed by the '708 patent, lenses were only single stage lenses with haptics going from the lens to muscle tissue. The '708 patent discloses multi-stage lenses that are stacked, with haptics traversing between each lens, connecting each lens together.

While conceptually an excellent idea, there remains a need in the art to improve the manufacture of such intraocular lenses, such as providing a mold and molding method for making such multi-stage lenses.

SUMMARY OF THE INVENTION

It is in view of the above problems that the present invention was developed. The invention is a mold and molding method for making a multi-stage intraocular lens. Specifically, the mold has a core with lens cavities, haptic cavities, and a gate in direct fluid communication with one or more of the cavities. In addition, the mold is provided with a gasket surrounding the core.

In use, molding material is flowed through the gate and into the cavities. As the silicone flows into the cavities, a vacuum is drawn around the core and through the gasket. The vacuum evacuates air trapped in the mold core and helps pull the molding material through the mold core.

Further features and advantages of the present invention, as well as the structure and operation of various embodiments of the present invention, are described in detail below with reference to the accompanying drawings.

BRIEF DESCRIPTION OF THE DRAWINGS

The accompanying drawings, which are incorporated in and form a part of the specification, illustrate the embodiments of the present invention and together with the description, serve to explain the principles of the invention. In the drawings.

DETAILED DESCRIPTION OF THE PREFERRED EMBODIMENTS

Figure 1:
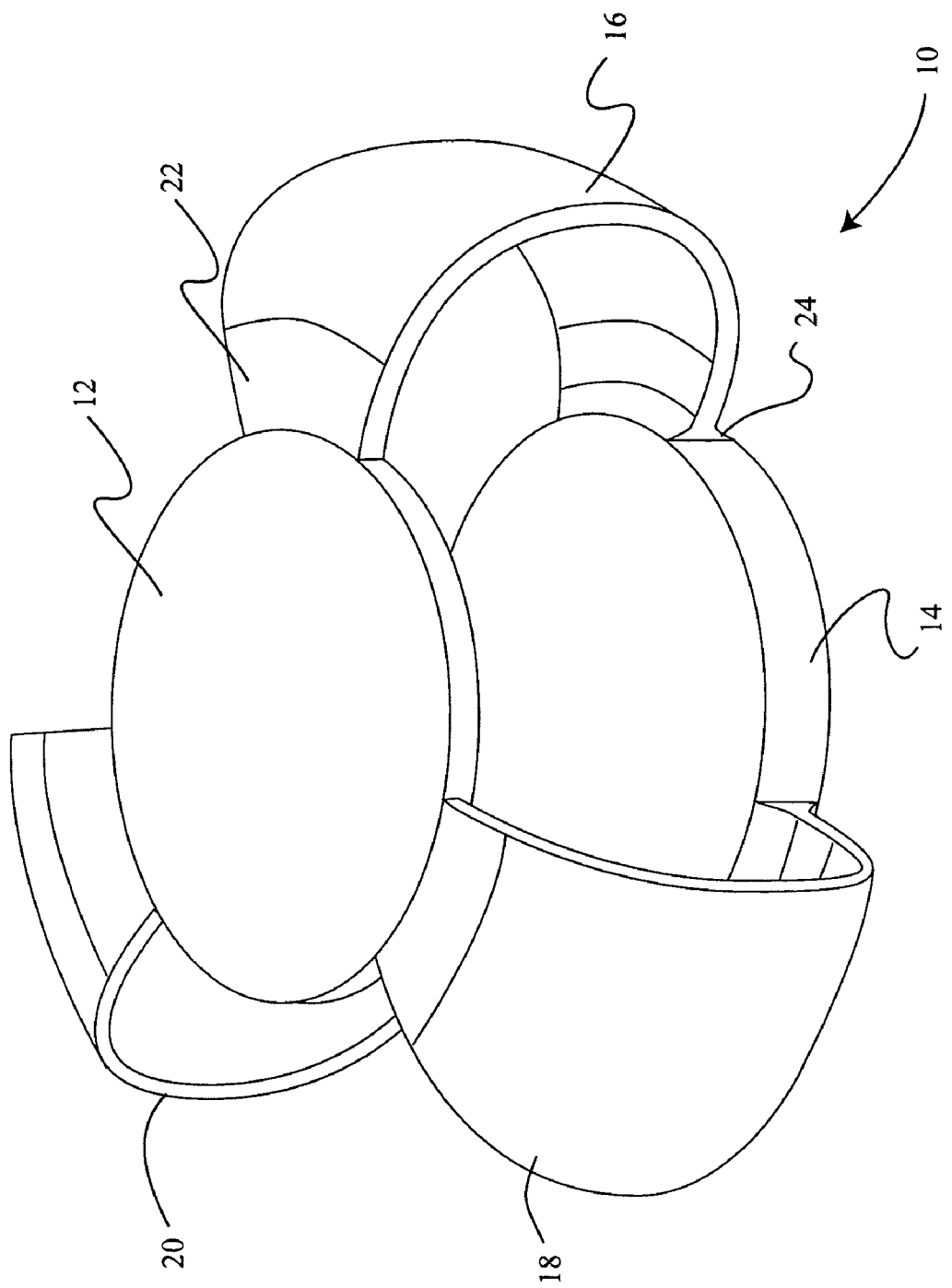
FIG. 1 is a perspective view of a multi-stage lens produced by the present invention.

Referring to the accompanying drawings in which like reference numbers indicate like elements, FIG. 1 illustrates a multi-stage intraocular lens, shown generally at 10, which is produced by the present invention. It is understood that lens 10 is shown with a pair of lenses, but that multi-stage lenses having more than two (2) lenses may be produced by the method of the present invention. The multi-stage lens 10 is provided with an anterior lens 12 and a posterior lens 14 that are connected by a first haptic 16, second haptic 18 and third haptic 20. The multi-stage lens 10 is preferably made from silicone. The haptics 16, 18, 20 are bendable, allowing the lenses 12, 14 to be adjusted relative to each other. The haptics 16, 18, 20 can connect the lenses 12, 14 at their periphery 22 or in their interior region 24.

Figure 2:
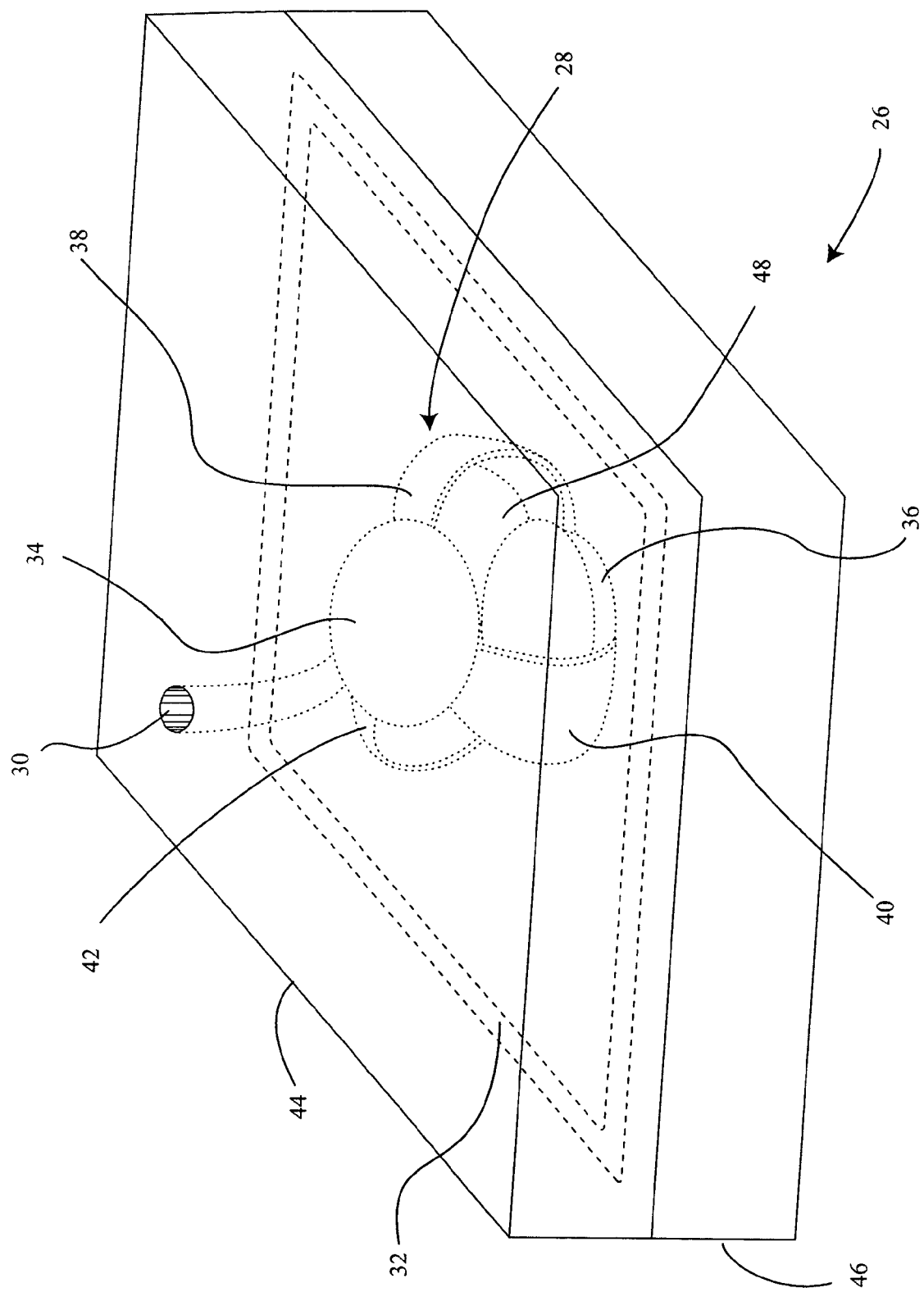
FIG. 2 is a perspective view of the mold, mold core, material gate, and gasket of the present invention.
Figure 3A:
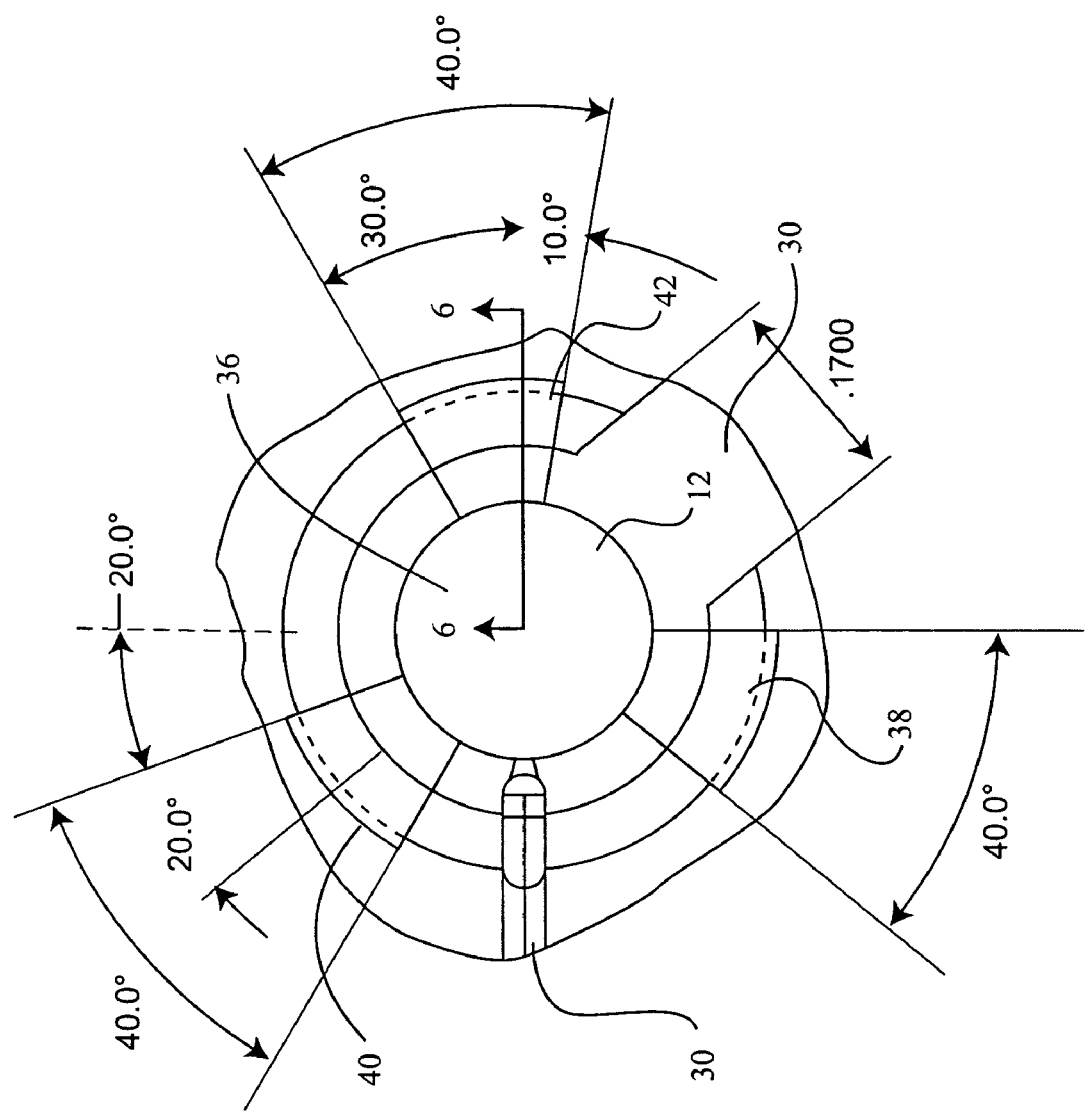
FIGS. 3A and 3B are top views of the mold core, illustrating the placement of the gate.

Turning now to FIG. 2, a mold, shown generally at 26, has a mold core 28, a material flow gate 30, and a gasket 32. The mold core 28 has a pair of lens cavities 34, 36 that are in communication with each other through haptic cavities 38, 40, 42. The gasket 32 surrounds the mold core 28, including the lens cavities 34, 36 and the haptic cavities 38, 40, 42. The material flow gate 30 is in communication with any one of more of the cavities in the mold core 28. Preferably, as illustrated in FIG. 3A, the material flow gate 30 is in communication with one mold core cavity, such as one of the lens cavities 34, 36, and spaced apart from the haptic cavities 38, 40, 42. The material flow gate 30 can also be in communication with multiple mold core cavities, including the haptic cavities 38, 40, 42. For example, as illustrated in FIG. 3B, the material flow gate 30 is in communication with one of the haptic cavities 38 as well as the lens cavity 36.

Figure 4:
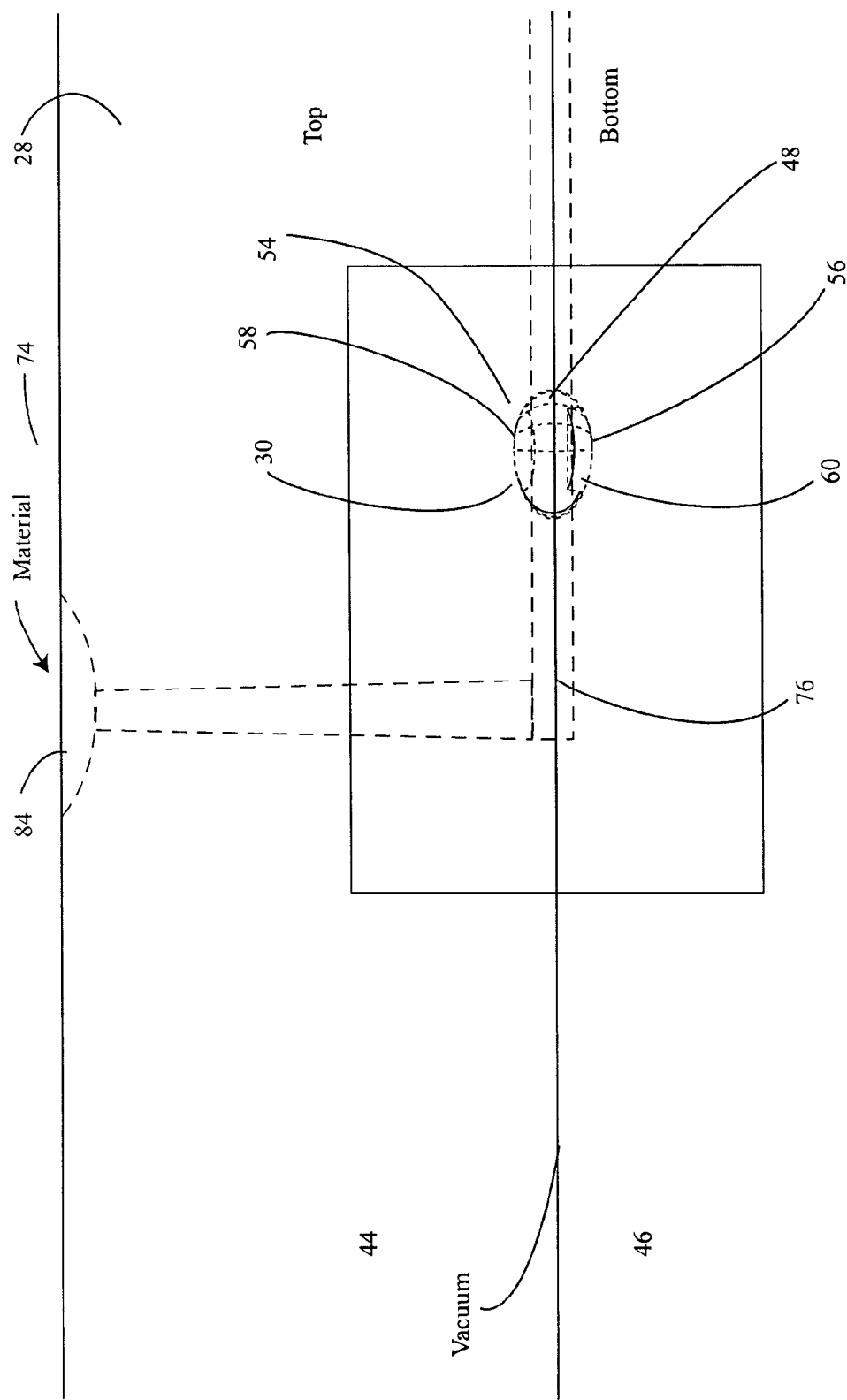
FIG. 4 is a side view of the mold core.
Figure 5A:
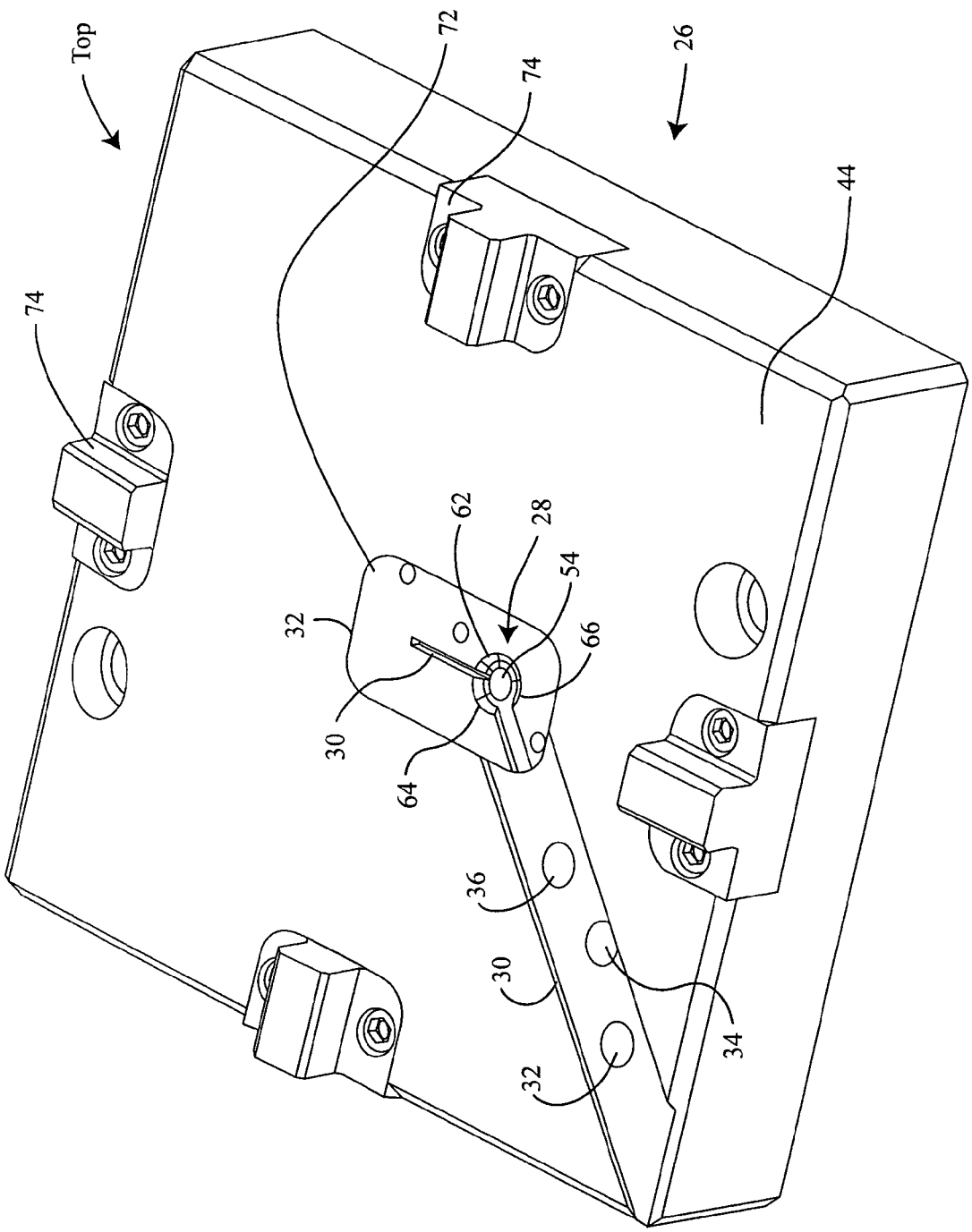
FIGS. 5A and 5B are perspective views of the mold core sections.
Figure 5B:
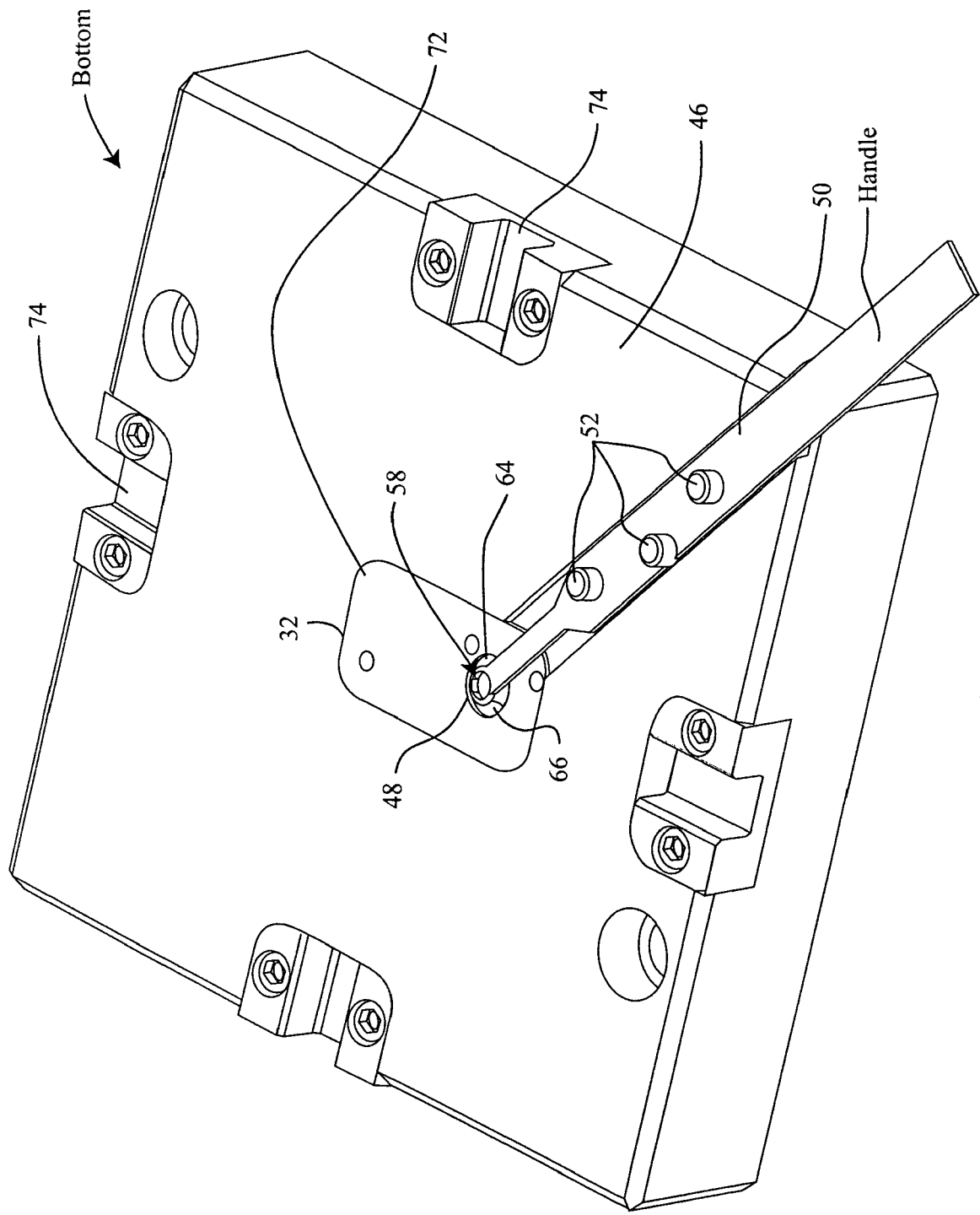

As illustrated in FIG. 4 and FIGS. 5A and 5B, the mold 26 can be formed by a pair of blocks 44, 46 that enclose a center block 48. FIG. 4 illustrates a side view of the mold core 28 with the center block 48 in place between the pair of blocks 44, 46. FIG. 5A illustrates the inner portion of the block 44 on one side of the mold 26, and FIG. 5B illustrates the inner portion of the block 46 on the opposite side of the mold 26 together with the center block 48. The center block is preferably connected to a handle 50 that extends through the blocks 44, 46. The handle 50 is equipped with offset pins 52 that guarantee the proper installation of the center block 48 into the mold 26, preventing the accidental insertion in a backwards or upside down orientation.

These views of the mold 26 in FIGS. 4, 5A and 5B show a particular embodiment of the mold core 28 in which exterior sides of the lens cavities 34, 36 are formed as recesses 54, 56 in the respective pair of blocks 44, 46. The interior sides of the lens cavities 34, 36 are enclosed by opposing sides 58, 60 of the center mold 48. Similarly the exterior sides of the haptic cavities 38, 40, 42 are formed by haptic recesses 62, 64, 66 in the pair of blocks 44, 46 while their interior sides are enclosed by the circumference 68 of the center mold. It will be appreciated that each one of the haptic recesses 62, 64, 66 has complementary recessed portions 70, 70' in the respective blocks 44, 46. Accordingly, the haptic recesses 62, 64, 66 in each one of the blocks 44, 46 are formed from a pair of partial haptic recesses in the blocks 44, 46 (i.e., complementary recessed portions 70, 70'). The interface between the complementary recessed portions 70, 70' should be identical in number, position and shape to reduce the potential for flashing and/or discontinuities in the haptics 16, 18, 20 during the molding process. The blocks 44, 46 fit together snugly at their complementary faces 72, 72' through hardware elements 74 that pull the blocks 44, 46 together. As particularly illustrated in FIG. 4, the material flow gate 30 is formed by a groove 76 in one of the blocks 44.

Figure 3B:
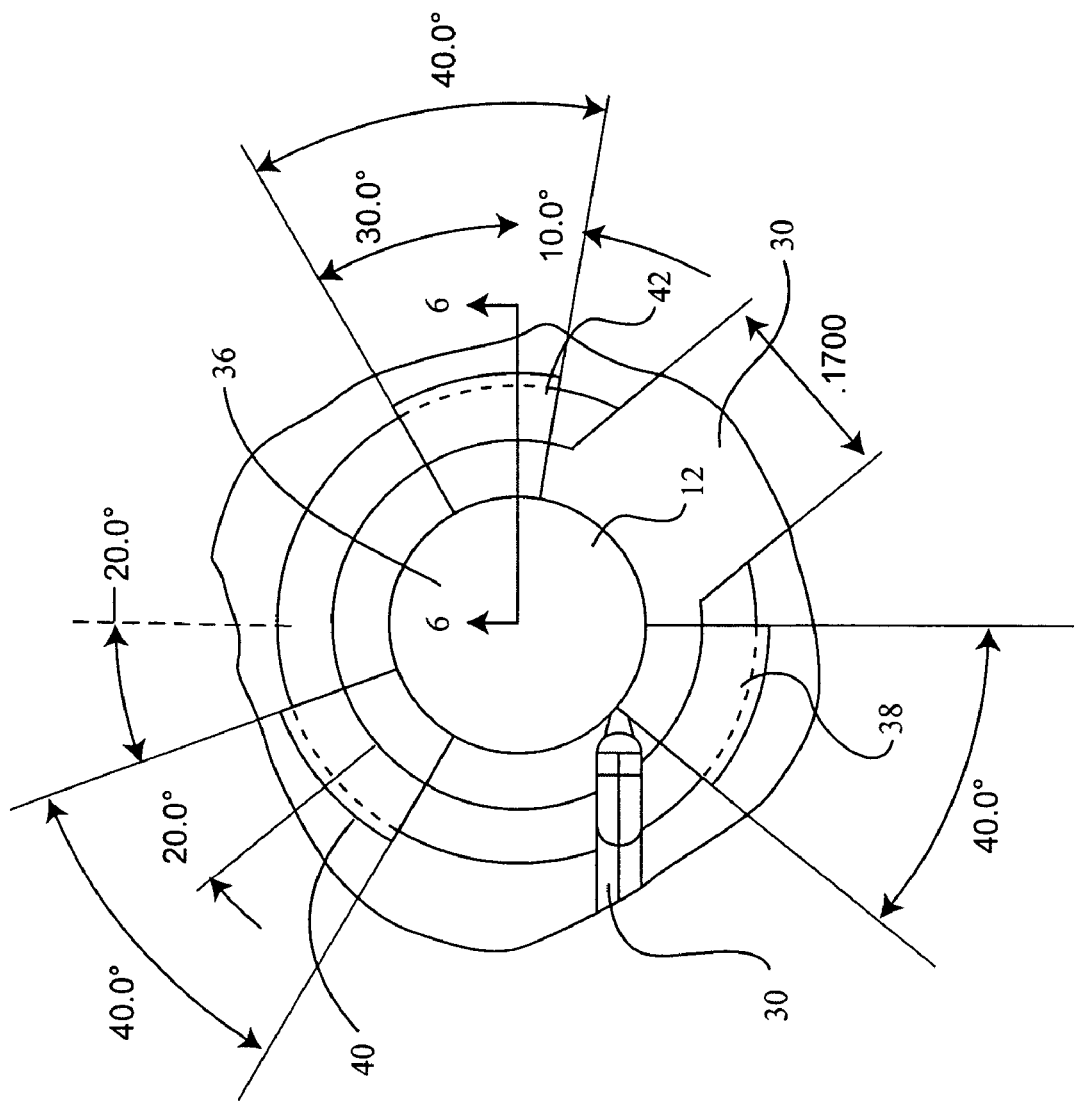
Figure 6B:
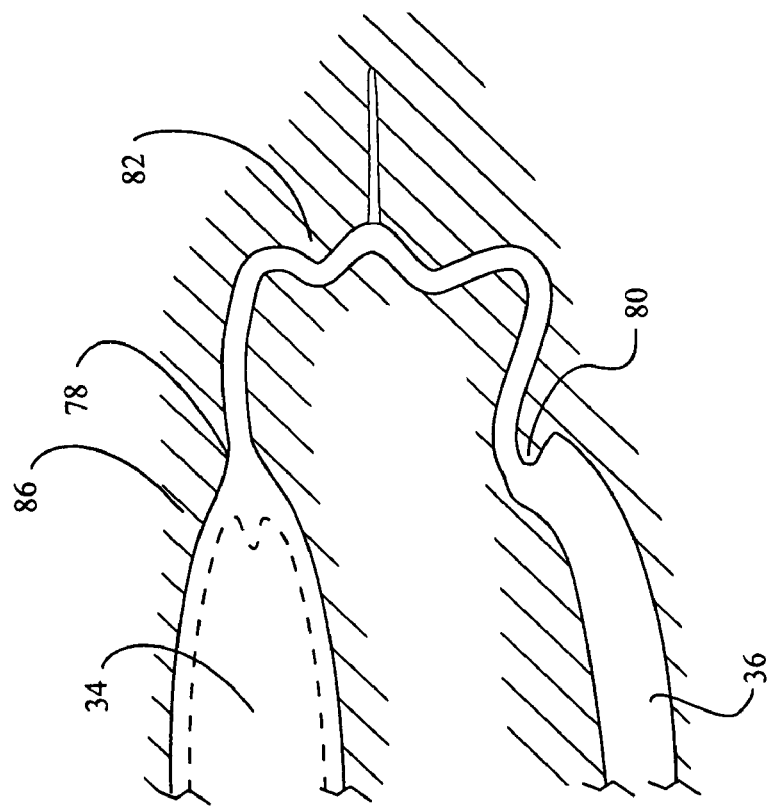
FIGS. 6A and 6B are partial cross-sectional views of the mold core illustrated in FIGS. 3A and 3B, respectively.
Figure 6A:
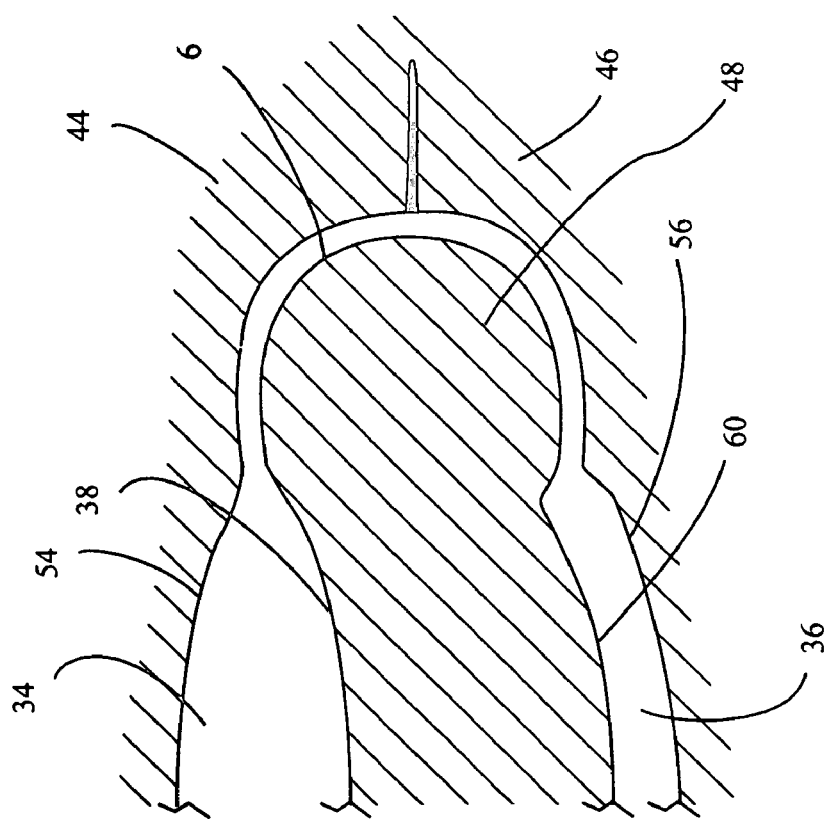

FIGS. 6A and 6B illustrate partial cross-sectional views of the mold core 28 according to FIGS. 3A and 3B, respectively. The shape of the haptics 16, 18, 20 and connection to the lenses 12, 14 can be changed through the use of different mold shapes. For example, the haptic cavities 38, 40, 42 may be in communication with the periphery 78 of a lens cavity 34 or an interior region 80 of a lens cavity 36. Similarly, the haptic cavities 38, 40, 42 could have an accordion cross-sectional shape 82.

In operation, the pair of blocks 44, 46 are locked in place while they enclose the center block 48. A molding material 84 is flowed through gate 30 into any one or more of the one mold core cavities. Then, a vacuum is applied to the mold core 28 through the gasket 42. The vacuum evacuates the air from the mold core cavities and assists the molding material 84 in flowing through all of the mold core cavities in the mold core 28.

In the preferred embodiment, the molding material 84 is silicone and first flows from the gate 30 into one lens cavity 34 and then flows into the other lens cavity 36 through the haptic cavities 38, 40, 42. It will be appreciated that, in an alternative embodiment, a lens 86 (see FIG. 6B) could be made out of a different material and placed in one or both of the lens cavities 34, 36. The lens 86 would at least partially fill one or both of the lens cavities 34, 36, and the molding material could flow around a portion of the lens 86. For example, the lens 86 could have attachment grooves or orifices where the molding material would lock into the lens 86. Such alternative lens materials could include polymethylmethacrylate (PMMA), glass, and acrylics. Generally, the molding material can be any type of transparent, pliable material, like silicone and hydrogel. Other possible materials include hydroxyethylmethacrylate (HEMA) and polydimethyl siloxanes.

In view of the foregoing, it will be seen that the several advantages of the invention are achieved and attained. The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. For example, a multi-stage lens having three stacked lenses separated by three haptics may also be manufactured by the present invention. In such a case, the gate 30 can be placed in direct fluid communication with one lens cavity 34. Then, material is flowed through gate 30 into the lens cavity 34. As the vacuum is applied through the gasket 32, material flows through each of the haptic cavities 38, 40, 42, and into the connected lens cavities. Thus, the breadth and scope of the present invention should not be limited by any of the above-described exemplary embodiments, but should be defined only in accordance with the following claims appended hereto and their equivalents.

What is claimed is:

1. A mold core for a multi-stage intraocular lens, comprising:
   a plurality of lens cavities;
   a plurality of haptic cavities in communication with said lens cavities;
   a material flow gate in direct communication with at least one of said haptic cavities; and
   a vacuum-sealing gasket surrounding said lens cavities and said haptic cavities.

2. The mold core according to claim 1, wherein said material flow gate is in direct communication with at least one of said lens cavities.

3. The mold core according to claim 1, wherein said haptic cavities are in communication with a periphery of said lens cavities.

4. The mold core according to claim 1, wherein said haptic cavities are in communication with an interior portion of said lens cavities.

5. The mold core according to claim 1, wherein said haptic cavities have an accordion cross-sectional shape.

6. The mold core according to claim 1, further comprising a handle having offset pins connected to said mold core.

7. The mold core according to claim 1, further comprising a preformed lens disposed in at least one of said lens cavities.

8. A mold core for a multi-stage intraocular lens, comprising:
   a first block having a face with a first lens recess and a plurality of partial haptic recesses extending between said first lens recess and said face;
   a second block having a second lens recess and a complementary face with a shape corresponding to said face of said first block and a plurality of complementary haptic recesses corresponding in number, position and shape to said partial haptic recesses of said first block, wherein said complementary haptic recesses extend between said second lens recess and said complementary face;
   a mold core between said first block and said second block, wherein said mold core encloses said first lens recess, said second lens recess and said haptic recesses to form a plurality of lens cavities and a plurality of haptic cavities extending between said plurality of lens cavities;
   a material flow gate in direct communication with at least one of said haptic cavities; and
   a vacuum-sealing gasket surrounding said first block and said second block.

9. The mold core according to claim 8, wherein said material flow gate is further comprised of a groove in said face of said first block.

10. The mold core according to claim 8, further comprising a handle having offset pins connected to said mold core.

11. The mold core according to claim 8, further comprising a pre-formed lens disposed in at least one of said lens cavities.

12. A mold core for a multi-stage intraocular lens, comprising:
   a plurality of lens cavities;
   a plurality of haptic cavities in communication with said lens cavities;
   a material flow gate in direct communication with at least one of said haptic cavities; and a vacuum-sealing gasket surrounding said lens cavities and said haptic cavities.

13. The mold core according to claim 12, wherein said material flow gate is in direct communication with at least one of said lens cavities.

14. The mold core according to claim 12, wherein said haptic cavities are in communication with a periphery of said lens cavities.

15. The mold core according to claim 12, wherein said haptic cavities are in communication with an interior portion of said lens cavities.

16. The mold core according to claim 12, wherein said haptic cavities have an accordion cross-sectional shape.

17. The mold core according to claim 12, further comprising a handle having offset pins connected to said mold core.

18. The mold core according to claim 12, further comprising a preformed lens disposed in at least one of said lens cavities.

19. A mold core for a multi-stage intraocular lens, comprising:
   a plurality of lens cavities;
   a plurality of haptic cavities in communication with said lens cavities;
   a material flow gate in direct communication with at least one mold core cavity, wherein said mold cavity is selected from the group consisting of lens cavities and haptic cavities; and
   a handle having offset pins connected to said mold core.

20. The mold core according to claim 19, further comprising a vacuum-sealing gasket surrounding said lens cavities and said haptic cavities.

21. The mold core according to claim 19, wherein said material flow gate is in direct communication with at least one of said haptic cavities.

22. The mold core according to claim 19, wherein said material flow gate is in direct communication with at least one of said lens cavities and at least one of said haptic cavities.

23. The mold core according to claim 19, wherein said haptic cavities are in communication with a periphery of said lens cavities.

24. The mold core according to claim 19, wherein said haptic cavities are in communication with an interior portion of said lens cavities.

25. The mold core according to claim 19, wherein said haptic cavities have an accordion cross-sectional shape.

26. The mold core according to claim 19, further comprising a preformed lens disposed in at least one of said lens cavities.

27. A mold core for a multi-stage intraocular lens, comprising:
   a first block having a face with a first lens recess and a plurality of partial haptic recesses extending between said first lens recess and said face;
   a second block having a second lens recess and a complementary face with a shape corresponding to said face of said first block and a plurality of complementary haptic recesses corresponding in number, position and shape to said partial haptic recesses of said first block, wherein said complementary haptic recesses extend between said second lens recess and said complementary face;
   a mold core between said first block and said second block, wherein said mold core encloses said first lens recess, said second lens recess and said haptic recesses to form a plurality of lens cavities and a plurality of haptic cavities extending between said plurality of lens cavities;
   a material flow gate in direct communication with at least one cavity in said mold core; wherein said mold cavity is selected from the group consisting of said lens cavities and said haptic cavities;
   a vacuum-sealing gasket surrounding said first block and said second block; and
   a handle having offset pins connected to said mold core.

28. The mold core according to claim 27, wherein said material flow gate is further comprised of a groove in said face of said first block.

29. The mold core according to claim 27, further comprising a pre-formed lens disposed in at least one of said lens cavities.

* * * * *